United States Patent
Gonzenbach et al.

[11] Patent Number: 6,123,929
[45] Date of Patent: Sep. 26, 2000

[54] LIGHT SCREENING COMPOSITION CONTAINING A POLYSILOXANE-TYPE UV-B SCREENING AGENT AND A BENZIMIDAZOL-TYPE SCREENING AGENT

[75] Inventors: Hans Ulrich Gonzenbach, Geneva; Ulrich Huber, Erlenbach; Rolf Schwarzenbach, Winterthur, all of Switzerland

[73] Assignee: Roche Vitamins Inc., Nutley, N.J.

[21] Appl. No.: 09/353,861

[22] Filed: Jul. 15, 1999

[30] Foreign Application Priority Data

Jul. 16, 1998 [EP] European Pat. Off. ............... 98113311

[51] Int. Cl.[7] ............... A61K 7/42; A61K 7/44; A61K 7/00
[52] U.S. Cl. ............... 424/59; 424/60; 424/400; 424/401
[58] Field of Search ............... 424/59, 60, 400, 424/401

[56] References Cited

U.S. PATENT DOCUMENTS 5,882,632  3/1999  Allard et al. ............... 424/59

FOREIGN PATENT DOCUMENTS

| | | |
|---|---|---|
| 358 584 A1 | 3/1990 | European Pat. Off. |
| 538 431 B1 | 2/1996 | European Pat. Off. |
| 813 857 A1 | 12/1997 | European Pat. Off. |
| 0 848 945 A1 | 6/1998 | European Pat. Off. |
| 0 860 165 A1 | 8/1998 | European Pat. Off. |
| 0 897 716 A2 | 2/1999 | European Pat. Off. |
| 197 04 990 A1 | 8/1997 | Germany. |
| 93/04665 | 3/1993 | WIPO. |
| 94/06404 | 3/1994 | WIPO. |

OTHER PUBLICATIONS

Derwent Abstract No. 98–04413 of EP 813 857 "Sun Protection Composition for use in Protection of Skin and Hair—Comprise Hydrophilic and Lipophilic Filter Compounds in Oil in Water Emulsion with Oil Phase of Mutually Incompatible Components of Polyol" (Dec. 29, 1997).

Derwent Abstract No. 99–134454 of EP 897 715 "Light Screening Component for Cosmetic or dermatological Preparation(s)—Involves Combination of Solid UV Filter and UV Filter Containing Siloxy Groups, to Enhance Protection Factor and Improve Dispersion" (Feb. 24, 1999).

Derwent Abstract No. 8190275 of EP 358 584 "Modified Diorganopolysiloxane Containing Benzalmalonate gp.—has High Refractive Index for Incorporation in Optical Fibres and also used as Lubricant for PVC" (Mar. 14, 1990).

*Primary Examiner*—Shelley A. Dodson
*Attorney, Agent, or Firm*—Mark E. Wadell; Stephen M. Haracz; Bryan Cave LLP

[57] ABSTRACT

The invention relates to a cosmetic light screening composition containing, in an aqueous phase, about 0.5% to about 10 wt % of 2-phenylbenzimidazol-sulphonic acid or a salt thereof and at least one fatty phase, including about 1% to about 30 wt % of a linear or cyclic polysiloxane compound of the general formula Ia or Ib:

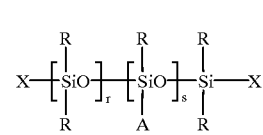

Ia

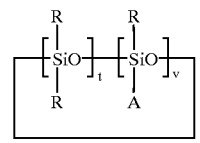

Ib wherein x is R or A;

A is a group selected from the formula IIa, IIb or IIc;

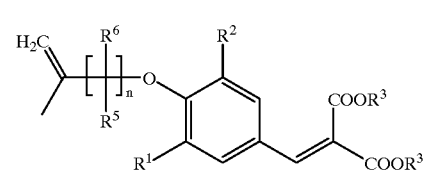

IIa

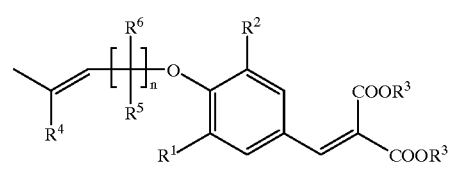

IIb

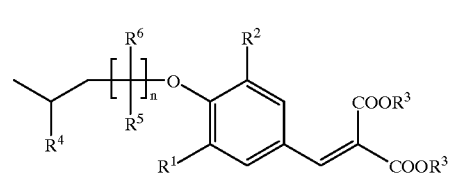

IIc

R is hydrogen, $C_{1-6}$ alkyl or phenyl;
$R^1$ and $R^2$ are each independently hydrogen, hydroxy, $C_{1-6}$-alkyl or $C_{1-6}$-alkoxy;
$R^3$ is $C_{1-6}$-alkyl;
$R^4$ is hydrogen or $C_{1-6}$-alkyl;
$R^5$ and $R^6$ are each independently hydrogen or $C_{1-6}$-alkyl;
r is from 0 to 250;
s is from 0 to 20;
r+s is at least 3;
t is from 0 to 10;
v is from 0 to 10;
v+t is at least 3;
n is from 1 to 6; and
when s is 0, at least one X is A. Methods of using such compositions are also provided.

14 Claims, No Drawings

LIGHT SCREENING COMPOSITION CONTAINING A POLYSILOXANE-TYPE UV-B SCREENING AGENT AND A BENZIMIDAZOL-TYPE SCREENING AGENT

FIELD OF THE INVENTION

The invention relates to photostable cosmetic light screening compositions for the protection of the human epidermis against ultraviolet rays of wavelengths between 280 and 320 nm (UV-B). In particular, the invention relates to cosmetic light screening compositions containing a lipophilic polysiloxane-type UV-B screening agent and a hydrophilic benzimidazole-type UV-B screening agent.

BACKGROUND OF THE INVENTION

In the European patent publication EP-0813857 (hereinafter "EP '857"), a sun protection composition having a synergistic UV-protection activity is reportedly described. This composition reportedly includes (a) a water phase, (b) two oil phases, (c) emollients for oil-in-water and water-in-oil type emulsions, (d) a hydrophilic UV-A filter (such as benzophenone derivatives) or a hydrophilic UV-B filter (such as benzimidazole derivatives), and (e) a lipophilic UV-A filter (such as 4-tert. butyl-4'-methoxydibenzoylmethane (PARSOL 1789®)) or a lipophilic UV-B filter (such as octocrylene (UVINUL N-539®)) or an organosiloxane filter (as described in WO 93/04665) or an organosiloxane filter of the benzotriazole type (as described in WO94/06404). This sun protection composition is reportedly characterized in that the first and second oil phases are incompatible.

EP '857 reportedly describes only generally that the combined filter substances have a synergistic ultraviolet protection activity without providing any guidance as to how to select a specific filter combination to reach a specific synergistic effect. Furthermore, the organosiloxanes as described in WO 93/04665 or WO94/06404 do not specifically refer to organosiloxanes containing a chromophore residue of the benzmalonate type.

BRIEF SUMMARY OF THE INVENTION

The present invention is a sunscreen composition containing a polysiloxane having a chromophore residue of the benzmalonate-type as a lipophilic UV-B screening agent and a hydrophilic benzimidazol-type UV-B screening agent. Such a composition provides synergistically enhanced protection indices.

More particularly, the present invention is a cosmetic light screening composition containing, in an aqueous phase, about 0.5% to about 10 wt % of 2-phenylbenzimidazol-sulphonic acid or a salt thereof, and at least one fatty phase, including about 1% to about 30 wt % of a linear or cyclic polysiloxane compound of the general formula Ia or Ib:

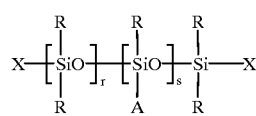

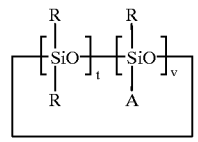

wherein

X is R or A;

A is a group selected from the formula IIa, IIb or IIc:

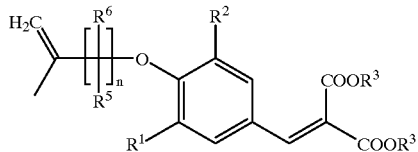

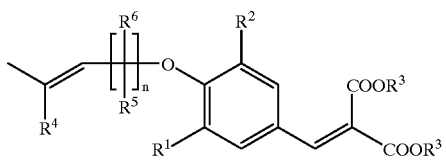

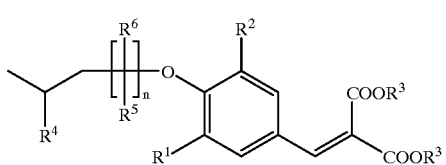

R is hydrogen, $C_{1-6}$ alkyl or phenyl;
$R^1$ and $R^2$ are each independently hydrogen, hydroxy, $C_{1-6}$-alkyl or $C_{1-6}$-alkoxy;
$R^3$ is $C_{1-6}$-alkyl;
$R^4$ is hydrogen or $C_{1-6}$-alkyl;
$R^5$ and $R^6$ are each independently hydrogen or $C_{1-6}$-alkyl;
r is from 0 to 250;
s is from 0 to 20;
r+s is at least 3;
t is from 0 to 10;
v is from 0 to 10;
v+t is at least 3; and
n is from 1 to 6.

In this composition when s is 0, at least one X is A.

Another embodiment is a cosmetic light screening composition that includes, in an aqueous phase, about 0.5% to about 5 wt % of 2-phenylbenzimidazol-sulphonic acid or a salt thereof, and at least one fatty phase, that includes about 2% to about 20 wt % of a linear polysiloxane compound of the general formula Ia as defined above wherein X is methyl;
A is a group selected from the formula IIa or IIb;
R is methyl;
$R^1$ and $R^2$ are hydrogen, methoxy or ethoxy, or one of $R^1$ and $R^2$ is hydrogen and the other is methyl, methoxy or ethoxy;
$R^3$ is methyl or ethyl;
$R^4$ is hydrogen or methyl;
$R^5$ and $R^6$ is hydrogen;

r is about 5 to about 150;

s is about 2 to about 10; and n is 1.

Another embodiment is a cosmetic light screening composition that includes, in an aqueous phase, about 1% to about 2 wt % of 2-phenylbenzimidazol-sulphonic acid or a salt thereof and at least one fatty phase that includes about 5 wt % of a linear polysiloxane compound of the general formula Ia as set forth above wherein $R^1$ and $R^2$ are hydrogen;

$R^3$ is ethyl;

$R^4$ is hydrogen;

r is a statistical mean of about 4; and s is a statistical mean of about 60.

Another embodiment is a method for screening ultraviolet radiation from a human's skin that includes applying to the skin an effective UV screening amount of the cosmetic light screening compositions set forth above.

DETAILED DESCRIPTION OF THE INVENTION

As used herein, the term "$C_{1-6}$-alkyl" refers to groups such as methyl, ethyl, propyl, isopropyl, butyl, sec. butyl, isobutyl, pentyl and neopentyl. As used herein, the term "$C_{1-6}$-alkoxy" refers to the corresponding alkoxy groups.

In the present invention, the R residues are preferably methyl. The $R^1$ and $R^2$ residues are preferably hydrogen, methoxy or ethoxy, more preferably hydrogen, or one of $R^1$ and $R^2$ is hydrogen and the other is methyl, methoxy or ethoxy. The $R^3$ residues are preferably methyl or ethyl, more preferably ethyl. Preferably, $R^4$ is hydrogen or methyl, $R^5$ and $R^6$ are hydrogen, and n is 1.

In the present invention, the salts of 2-phenylbenzimidazol-sulphonic acid that may be used include alkali salts, such as sodium- or potassium salts, ammonium salts, morpholine salts, salts of primary, sec., and tert. amines, such as monoethanolamine salts, diethanolamine salts, and the like.

The polysiloxane compounds having a group A of the general formula IIa and IIb and their preparation are described in the EP 0538431, which is incorporated by reference as if recited in full herein. These polysiloxane compounds are preferred.

The polysiloxane compounds having a group A of the general formula IIc and their preparation are described in the EP 0358584, which is incorporated by reference as if recited in full herein.

In the linear polysiloxane compounds according to formula Ia, the chromophore carrying residue (A) may be connected to the end groups of the polysiloxane (X=A) or may be statistically distributed. Linear polysiloxane compounds wherein the chromophore-carrying residue A is statistically distributed are preferred. These polysiloxane compounds have at least one unit carrying the chromophore residue (s=1). In these compounds, it is preferred that "s" have a value of from about 2 to about 10, such as a statistical mean of about 4. The number of the other silicone units ("r") present in the polysiloxane compounds is preferably about 5 to about 150, such as for example, a statistical mean of about 60.

For cosmetic uses, polysiloxane compounds with 20% or less, such as for example, less than 10%, of the total siloxane units carrying a chromophore residue are preferred.

In the present invention, the ratio of polysiloxane units having a chromophore residue A of the formula IIa to those having a chromophore residue A of the formula IIb is not critical. This ratio may be about 1:1 to about 19:1, preferably about 2:1 to about 9:1, such as for example about 4:1.

The concentration of the polysiloxane compound in the cosmetic light screening composition is preferably about 2% to about 20 wt %, such as for example about 5 wt %. The concentration of 2-phenylbenzimidazol sulphonic acid or a salt thereof is preferably about 0.5% to about 5 wt %, such as for example about 1% to 2 wt %. The ratio of 2-phenylbenzimidazol sulphonic acid or a salt thereof to the polysiloxane compound as defined above is not critical. For example, the ratio is about 1:1 to about 1:20, preferably about 1:5.

Thus, one embodiment of the present invention is a cosmetic light screening composition that contains, in an aqueous phase, about 0.5% to about 5 wt % of 2-phenylbenzimidazol-sulphonic acid or a salt thereof, and at least one fatty phase, including about 2% to about 20 wt % of a linear polysiloxane compound of the general formula Ia, wherein X is methyl;

A is a group selected from the formula IIa or IIb;

R is methyl;

$R^1$ and $R^2$ are hydrogen, methoxy or ethoxy, or one of $R^1$ and $R^2$ is hydrogen and the other is methyl, methoxy or ethoxy;

$R^3$ is methyl or ethyl;

$R^4$ is hydrogen or methyl;

$R^1$ and $R^6$ are hydrogen;

r is about 5 to about 150;

s is about 2 to about 10; and n is 1.

Another embodiment is a cosmetic light screening composition that contains, in an aqueous phase, about 1% to about 2 wt % of 2-phenylbenzimidazol-sulphonic acid or a salt thereof and at least one fatty phase, including about 5 wt % of a linear polysiloxane compound of the general formula Ia wherein X is methyl;

A is a group selected from the formula IIa or IIb;

R is methyl;

$R^1$ and $R^2$ are hydrogen;

$R^3$ is ethyl;

$R^4$ is hydrogen;

$R^5$ and $R^6$ are hydrogen;

r is a statistical mean of about 4;

s is a statistical mean of about 60; and n is 1.

The polysiloxane compounds Ia or Ib wherein A is a residue of the formula IIa or IIb may be prepared as described in EP 0538431 by silylation of the corresponding benzalmalonates according to the following reaction scheme:

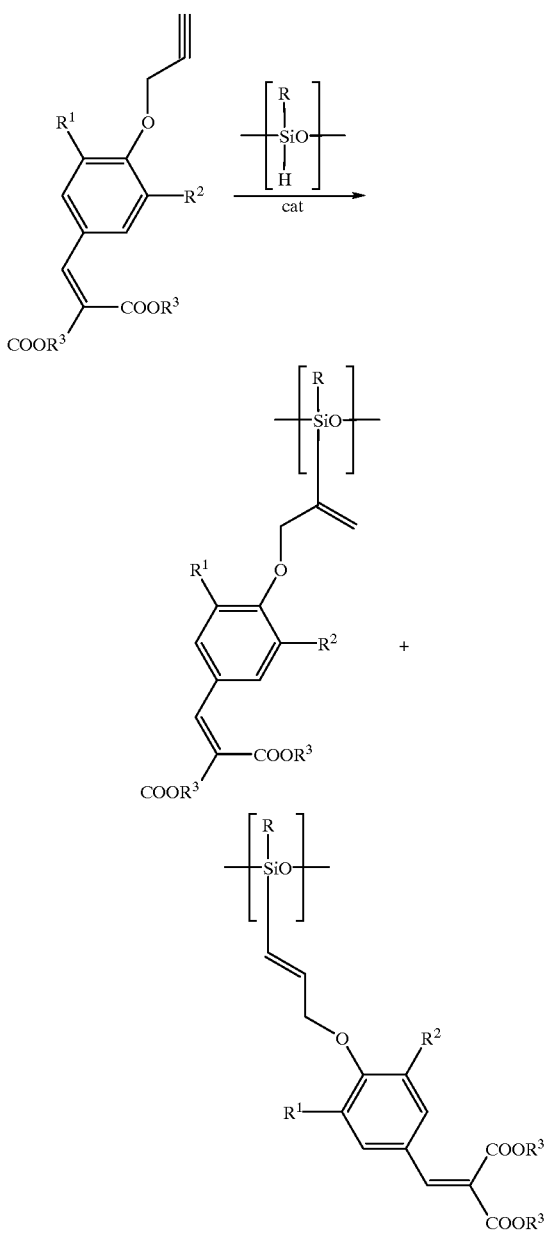

wherein R, $R^1$, $R^2$, and $R^3$ are as defined above, and "cat" refers to a catalyst as described in more detail below.

The silylation of the 4-(2-propynylox)phenyl methylene diethylester may be carried out employing known procedures for the addition of silicon bonded hydrogen atoms to groups containing aliphatic unsaturation. Such reactions are generally catalyzed (cat) by a platinum group metal or a complex of such a metal. Examples of catalysts which may be employed are platinum on carbon, chloroplatinic acid, platinum acetyl acetonate, complexes of platinum compounds with unsaturated compounds, e.g. olefins and divinyl disiloxanes, complexes of rhodium and palladium compounds, and complexes of platinum compounds supported on inorganic substrates. The addition reaction may be performed at reduced, atmospheric, or increased pressure. A solvent may be used, e.g. toluene or xylene, in the reaction mixture although the presence of the solvent is not essential. It is also preferred to carry out the reaction at elevated reaction temperatures, e.g. from about 50° C. up to about 150° C.

The production of the novel light screening compositions of the present invention includes incorporating a polysiloxane compound as defined above and 2-phenylbenzimidazol-sulphonic acid or a salt thereof optionally in combination with other known UV-A and/or UV-B filters, in a cosmetic base which is usual for light screening agents.

UV B filters suitable for use in the present invention have absorption maxima between about 290 and 320 nm. In the present invention, suitable UV B filters include the following organic compounds: p-Aminobenzoic acid derivatives, such as ethyl-, propyl-, butyl-, and isobutyl p-aminobenzoate and the like; Acrylates, such as 2-ethylhexyl 2-cyano-3,3-diphenylacrylate (octocrylene), ethyl 2-cyano-3,3-diphenylacrylate and the like; Aniline derivatives, such as methyl anilinum methosulfate and the like; Anthranilic acid derivatives, such as methyl anthranilate and the like; Benzophenone derivatives, such as benzophenone-3, benzophenone-4 and the like; Camphor derivatives, such as methyl benzylidene camphor (PARSOL 5000), 3-benzylidene camphor, camphor benzalkonium methosulfate, polyacrylamidomethyl benzylidene camphor, sulfa benzylidene camphor, sulphomethyl benzylidene camphor, therephthalidene dicamphor sulfonic acid and the like; Cinnamate derivatives, such as octyl methoxycinnamate (PARSOL MCX) or ethoxyethyl methoxycinnamate and the like, as well as cinnamic acid derivatives bonded to siloxanes; Gallic acid, such as digalloyl trioleate and the like; Salicylate derivatives, such as isopropylbenzyl salicylate, benzyl salicylate, butyl salicylate, octyl salicylate (Neo Heliopan OS), isooctyl salicylate or homomethyl salicylate (homosalate, Heliopan) and the like; Triazole derivatives, such as hydroxyphenylbenztriazole, 2-2'methylene-bis-(6-(2H-benzotriazole-2-yl)-4-(1,1,3,3,-tetramethylbutyl)-phenol (TINOSORB M) and the like; and Triazone derivatives, such as octyl triazone (Uvinul T-150), dioctyl butamido triazone (Uvasorb HEB) and the like.

The present light screening compositions may also include pigments, such as microparticulated $TiO_2$, ZnO, and the like. As used herein, the term "microparticulated" means a particle size from about 5 to about 200 nm, preferably from about 15 nm to about 100 nm. The microparticulated compounds (i.e., $TiO_2$ particles) may also be coated with (a) metal oxides such as for example, aluminum or zirconium oxides, and (b) organic coatings such as for example, polyols, methicone, aluminum stearate, and alkyl silane.

The formulation of the present invention may further contain UV-A filters, such as for example, Dibenzoyl-methane derivatives including 4-tert. butyl-4'-methoxydibenzoyl-methane and the like; and Triazine compounds, including those described in the following European Patent Publications: EP 0693483, EP 0704437, EP 0704444, and EP 0780382. Such triazine compounds include for example, 2,2'-[6-(4-methoxyphenyl)-1,3,5-triazine-2,4-diyl]bis[5-[2-ethylhexyl) oxy]- which is available under the tradename TINOSORB S (Ciba Speciality Chemicals Holding Switzerland).

In the present invention, conventional cosmetic bases typically combined with light screening compositions may be used. Moreover, the compositions of the present invention are prepared using conventional techniques which will correspond to the particular cosmetic requirements, e.g. creams, lotions, emulsions, salves, gels, solutions, sprays, sticks and milks. Such conventional formulations and methods may also be found in, e.g., Sunscreens, Development, Evaluation and Regulatory Aspects, ed. N.Y. Lowe, N. A. Shaath, Marcel Dekker, Inc. New York and Basel, 1990, which is hereby incorporated by reference as if recited in full herein.

The present invention also includes a method for screening UV radiation from a human's skin. This method includes applying to the skin of a human an effective amount of a UV screening composition according to the present invention in a cosmetic base to, e.g., protect against damage to the epidermis caused by UV radiation in the 280–320 nm (UV-B) range. An "effective amount" of a composition according to the present invention may be 1.5 mg sunscreen composition/cm² skin.

The following examples are provided to further illustrate methods of preparation of the light screening compositions of the present invention, as well as certain physical properties thereof. These examples are illustrative only and are not intended to limit the scope of the invention in any way.

EXAMPLES

Example 1

In this example propanedioic {(4-[2-propynyloxy)phenyl] methylene} diethylester as described in EP 0538431 was prepared.

To a stirred suspension of 4-hydroxybenzaldehyde (425.8 g) and $K_2CO_3$ (807.6 g) in acetone (2.96 ml) at a reflux temperature of about 60° C. under a nitrogen atmosphere, was added dropwise 3-bromo-propyne (502.4 g) over a period of two hours. The reaction was heated at reflux for more than 3 hours. After cooling to room temperature, the reaction mixture was filtered, and excess $K_2CO_3$ was removed. The reaction mixture was then washed several times with acetone.

The filtrate was washed with a saturated aqueous solution of $NaHCO_3$ and NaCl. The aqueous phase was extracted with diethylether. The combined organic extracts were dried over $Na_2SO_4$, filtered, and concentrated to a volume of 1 l. The solution was kept at about 4° C. in the refrigerator overnight. The crystals were filtered out and washed with cold diethyl ether. The filtrate was kept in the refrigerator and when more crystals formed, they were removed. This procedure was repeated 3 times resulting in 1,385 g of 4-(2-propynyloxy) benzaldehyde in 83% yield. The material was analyzed by gas chromatography, and shown to be 99.9% pure.

The resulting compound (449.2 g) was added in small amounts to a stirred solution of diethylmalonate (448.5 g), piperidine (23.84 g), toluene (1,400 ml) and acetic acid (59 g) at about 50° C. The acetic acid was added in three equal portions after 1, 1.5, and 2 hours, respectively. The reaction mixture was heated to reflux. After four hours, the mixture was allowed to cool to room temperature and was washed with a saturated aqueous solution of $NaHCO_3$ and NaCl. The mixture was then dried with $Na_2SO_4$, filtered and concentrated, giving 853.4 g of a dark brown oily product.

Diethylether (458 ml) and n-hexane (358 ml) were added to the product and the solution was kept in the refrigerator overnight. The solution was filtered, giving 564.8 g of light brown crystals (67% yield) having a melting point of 45.5° C. to 48° C. Recrystallisation in ethanol and n-hexane yielded 543 g of the title compound as light brown crystals. The material was analyzed by gas chromatography, and shown to be 99.9% pure.

Example 2

This example demonstrates the preparation of an organosiloxane compound of the general formula Ia wherein R is methyl, s is 0, r is 20, X is A which is a benzalmalonate residue of the formula IIa and IIb wherein $R^1$ and $R^2$ are hydrogen, $R^3$ is ethyl and $R^4$, $R^5$ and $R^6$ are hydrogen, and n is 1 as described in EP 053 431 B 1.

5 g of {[4-(2-propynyloxy)phenyl]methylene}-diethyl ester were dissolved in 20 g of toluene and heated under nitrogen to about 80° C. 13.2 g of a hydrosiloxane having a degree of polymerization of 20 and 10 mpc SiH groups (3.62.% SiH) were then added dropwise after a platinum-divinyl-tetramethyl-disiloxane complex was added, giving $10^{-4}$ mole of Pt per mole of SiH of the hydrosiloxane. The mixture was heated to reflux and maintained at that temperature until all SiH groups were undetectable using infrared spectroscopic analysis. The mixture was then allowed to cool to room temperature. The toluene was then evaporated. After washing, 16.5 g of a slightly brown polymer was left having the average structure A-$[(CH_3)_2SiO]_{20}$-A, wherein A is a residue of the formula $IIa_1$ and $Ib_1$:

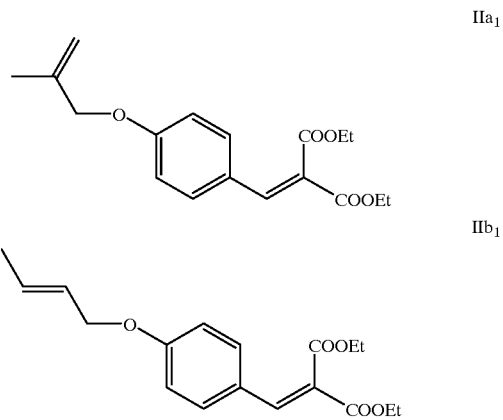

Example 3

This example demonstrates the preparation of an organosiloxane compound having the general formula Ia wherein R is methyl, r is 59, s is 4, X is methyl and A is a benzalmalonate residue of the formula IIa and IIb, wherein $R^1$ and $R^2$ are hydrogen, $R^3$ is ethyl, $R^4$, $R^5$ and $R^6$ are hydrogen as described in EP 0709080.

13.28 g of {[4-(2-propynyloxy)phenyl]methylene}-diethyl ester were dissolved in 75 g of toluene and heated under nitrogen to about 70° C. 44 g of a hydrosiloxane having a degree of polymerization of 65 and 6 mpc SiH groups (2.36% SiH) were then added dropwise after a platinum-divinyl-tetramethyl-disiloxane complex was added, giving $10^{-4}$ mole of Pt per mole of SiH of the hydrosiloxane. The mixture was heated to reflux and maintained at that temperature until all SiH were undetectable using infrared spectroscopic analysis. It was then allowed to cool to room temperature. The toluene was then evaporated. After washing, 52 g of a brown, viscous polymer was left having the average structure $(CH_3)_3SiO$—$[(CH_3)_2SiO]_{59}$-$[(CH_3)ASiO]_4$-$Si(CH_3)_3$, wherein A has the formula $IIa_1$ and $IIb_1$:

IIa₁

[Structure: CH₂=C(CH₃)-CH₂-O-C₆H₄-CH=C(COOEt)(COOEt)]

IIb₁

[Structure: CH₃-CH=CH-CH₂-O-C₆H₄-CH=C(COOEt)(COOEt)]

The ratio of compounds having a residue IIa₁ to compounds having a residue IIb₁ was about 4:1.

Example 4

In this example, cosmetic light screening compositions of the present invention are prepared.

A sunscreen O/W lotion containing 5wt % of a polysiloxane of formula Ia according to Example 3 and 1 wt % of 2-phenylbenzimidazol-sulphonic acid was prepared using the ingredients set forth in Table 1 below:

TABLE 1

| Part | % w/w | Ingredient | CTFA Name |
|------|-------|------------|-----------|
| A | 2.5 | Arlacel 60 sold by ICI | Sorbitan Stearate |
|   | 17.5 | Witconol APM sold by Witco | PPG-3 Myristylether |
|   | 1.0 | Stearyl alcohol | Stearyl alcohol |
|   | 5.0 |  | Polysiloxane |
|   | 5.0 | Silicon oil | Dimethicone 200/100 |
| B | 1.0 | PBSA | Phenylbenzimidazolsulfonicacid |
|   | 1.8 | NaOH 10% | Sodium Hydroxide |
|   | 2.5 | Tween 60 | Polysorbate 60 |
|   | 0.3 | Keltrol sold by Kelco UK | Xanthan Gum |
|   | 61.4 | Water |  |
| C | 2.0 | Sepigel 305 sold by Seppic | Polyacrylamid & C13-14 isoparaffin + laureth-7 |

CTFA: Cosmetic, Toiletry and Fragrance Association.
Part A: Added to and melted in the reactor.
Part B: mixed, nutralized and heated on a hotplate to 85° C.
Part C: added at 50° C.

Example 5

In this example, the Sun Protection Factor (SPF) of compositions of the present invention was determined.

The determination of the SPF was performed according to the COLIPA protocol (the European Cosmetic, Toiletry and Perfumery Association, Sun Protection Factor Test method, October 1994), which is incorporated by reference as if recited in full herein. A solar simulator SU 2000 having a lamp intensity in the range of 5.0 to 5.5 mW/cm² was used. The irradiation area was 6×1 cm², and the dose progression was 25%. The following UV filters were formulated using the cosmetic base set forth in Example 4 to yield a stable sunscreen lotion with identical distribution characteristics. An application dose of 2 mg/cm² was used according to the COLIPA protocol for in vivo SPF measurements in humans, on an application area of 50 cm².

The following sunscreen compositions were tested according to the procedure set forth above:

(1) A sunscreen composition containing a polysiloxane compound according to Example 3 and a second lipophilic UV-B filter, namely 2-ethylhexyl-p-methoxycinnamate (OMC) (available under the trade name PARSOL MCX); and (2) A sunscreen composition containing a polysiloxane compound according to Example 3 and a second hydrophilic UV-B filter, namely the diethanolamine salt of p-methoxycinnamatic acid (MC-DEA) (available under the tradename PARSOL Hydro).

The results are set forth in Table 2 below:

TABLE 2

| UV-Filter | In vivo SPF | Expected SPF | Synergy |
|-----------|-------------|--------------|---------|
| 10 wt % P3 | 4.7 | | |
| 2 wt % PBSA | 6.8 | | |
| 5 wt % P3 + 1 wt % PBSA | 8.1 | 5.8 | 40% |
| Comparative | | | |
| 10 wt % P3 | 4.7 | | |
| 2 wt % OMC | 5.3 | | |
| 5 wt % P3 + 1 wt % OMC | 5.8 | 5.0 | 16% |
| 10 wt % P3 | 4.7 | | |
| 2 wt % MC-DEA | 4.2 | | |
| 5 wt % P3 + 1 wt % MC-DEA | 4.8 | 4.5 | 7% |

P3: Polysiloxane according to Example 3.
PBSA: 2-phenylbenzimidazol-sulphonic acid
OMC: 2-ethylhexyl-p-methoxycinnamate
MC-DEA: diethanolamine salt of p-methoxycinnamatic acid.
In vivo SPF: Mean value of determination on 5 volunteers.
Expected SPF: Calculated value by adding in vivo SPF-value of 10 wt % P3 (4.7) to the in vivo SPF value of 2 wt % of the corresponding value for the other filters, divided by 2.
Synergy % deviation of in vivo SPF from expected (calculated) SPF.

The combination of PBSA and the polysiloxane according to the invention showed a surprising and unproportional increase of the SPF. Usually, the SPF of filter combinations is very close to the calculated value from the performance of the single filters, therefore, an unexpected synergistic effect was demonstrated using this combination.

The invention being thus described, it will be obvious that the same may be varied in many ways. Such variations are not to be regarded as a departure from the spirit and scope of the invention and all such modifications are intended to be included within the scope of the following claims.

We claim:

1. A cosmetic light screening composition comprising, in an aqueous phase, about 0.5% to about 10 wt % of 2-phenylbenzimidazol-sulphonic acid or a salt thereof and at least one fatty phase, comprising about 1% to about 30 wt % of a linear or cyclic polysiloxane compound of the general formula Ia or Ib:

Ia $$X-\left[\underset{R}{\overset{R}{SiO}}\right]_r\left[\underset{A}{\overset{R}{SiO}}\right]_s\underset{R}{\overset{R}{Si}}-X$$

-continued

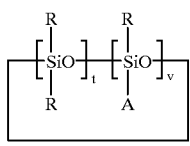

wherein
X is R or A;
A is a group selected from the formula Ia, IIb or IIc;

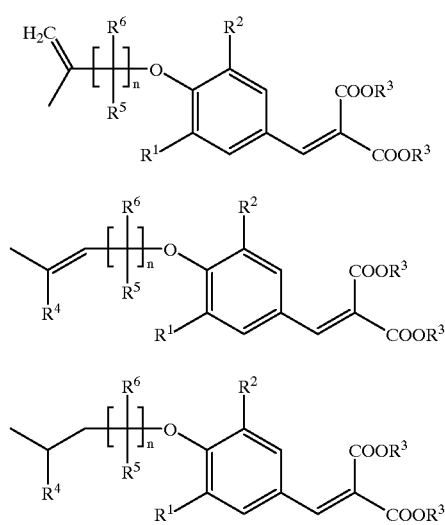

R is hydrogen, $C_{1-6}$ alkyl or phenyl;
$R^1$ and $R_2$ are each independently hydrogen, hydroxy, $C_{1-6}$-alkyl or $C_{1-6}$-alkoxy;
$R^3$ is $C_{1-6}$-alkyl;
$R^4$ is hydrogen or $C_{1-6}$-alkyl;
$R^5$ and $R^6$ are each independently hydrogen or $C_{1-6}$-alkyl;
r is from 0 to 250;
s is from 0 to 20;
r+s is at least 3;
t is from 0 to 10;
v is from 0 to 10;
v+t is at least 3;
n is from 1 to 6; and
when s is 0, at least one X is A.

2. A cosmetic light screening composition according to claim 1 wherein A is a residue of the formula IIa or IIb.

3. A cosmetic light screening composition according to claim 1 wherein the ratio of the organosiloxane compounds having a chromophore residue of the formula IIa to the organosiloxane compounds having a chromophore residue of the formula IIb is about 1:1 to about 19:1.

4. A cosmetic light screening composition according to claim 1 wherein the ratio of the organosiloxane compounds having a chromophore residue of the formula IIa to the organosiloxane compounds having a chromophore residue of the formula IIb is about 2:1 to about 9:1.

5. A cosmetic light screening composition according to claim 1 wherein the ratio of the organosiloxane compounds having a chromophore residue of the formula IIa to the organosiloxane compounds having a chromophore residue of the formula IIb is about 4:1.

6. A cosmetic light screening composition according to claim 1 wherein R is methyl.

7. A cosmetic light screening composition according to claim 1 wherein $R^1$ and $R^2$ are selected from the group consisting of hydrogen, methoxy, and ethoxy.

8. A cosmetic light screening composition according to claim 1 wherein one of $R^1$ and $R^2$ is hydrogen and the other is methyl, methoxy or ethoxy.

9. A cosmetic light screening composition according to claim 1 wherein $R^3$ is methyl or ethyl.

10. A cosmetic light screening composition according to claim 1 wherein $R^4$ is hydrogen or methyl, $R^5$ and $R^6$ are hydrogen and, n is 1.

11. A cosmetic light screening composition according to claim 1 comprising, in an aqueous phase, about 0.5% to about 5 wt % of 2-phenylbenzimidazol-sulphonic acid or a salt thereof, and at least one fatty phase, comprising about 2 to about 20 wt % of a linear polysiloxane compound of the general formula Ia wherein
X is methyl;
A is a group of the formula IIa or IIb;
R is methyl;
$R^1$ and $R^2$ are hydrogen, methoxy or ethoxy, or one of $R^1$ and $R^2$ is hydrogen and the other is methyl, methoxy or ethoxy;
$R^3$ is methyl or ethyl;
$R^4$ is hydrogen or methyl;
$R^5$ and $R^6$ is hydrogen;
r is about 5 to about 150;
s is about 2 to about 10; and
n is 1.

12. A cosmetic light screening composition according to claim 11 comprising, in an aqueous phase, about 1% to about 2 wt % of 2-phenylbenzimidazol-sulphonic acid or a salt thereof and at least one fatty phase comprising about 5 wt % of a linear polysiloxane compound of the general formula Ia, wherein
$R^1$ and $R^2$ are hydrogen;
$R^3$ is ethyl;
$R^4$ is hydrogen;
r is a statistical mean of about 4; and
s is a statistical mean of about 60.

13. A cosmetic light screening composition according claim 1 wherein said composition further comprises UV-A and/or UV-B filters.

14. A method for screening ultraviolet radiation from a human's skin comprising applying to the skin an effective UV screening amount of the composition according to claim 1 in a cosmetic base.

* * * * *

UNITED STATES PATENT AND TRADEMARK OFFICE
CERTIFICATE OF CORRECTION

PATENT NO. : 6,123,929
DATED : September 26, 2000
INVENTOR(S) : Hans Ulrich Gonzenbach, et al.

It is certified that error appears in the above-identified patent and that said Letters Patent is hereby corrected as shown below:

<u>Title page,</u>
Under [73] Assignee, please change "Nutley" to -- Parsippany --.
Under [57] ABSTRACT, second column, delete from "wherein" to "at least one X is A."
Under [56] References Cited, Other Publications, please insert the following:
-- Derwent English language abstract of EP 0 897 716 A2
Derwent English language abstract of DE 197 04 990 A1
Derwent English language abstract of EP 0 860 165 A1 --.

Signed and Sealed this

Eighteenth Day of September, 2001

*Attest:*

NICHOLAS P. GODICI
*Attesting Officer*   *Acting Director of the United States Patent and Trademark Office*